United States Patent
Shriram et al.

(10) Patent No.: US 11,810,294 B2
(45) Date of Patent: Nov. 7, 2023

(54) ULTRASOUND IMAGING SYSTEM AND METHOD FOR DETECTING ACOUSTIC SHADOWING

(71) Applicant: GE Precision Healthcare LLC, Wauwatosa, WI (US)

(72) Inventors: Krishna Seetharam Shriram, Bangalore (IN); Chandan Kumar Aladahalli, Bangalore (IN); Vikram Melapudi, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 200 days.

(21) Appl. No.: 17/214,026

(22) Filed: Mar. 26, 2021

(65) Prior Publication Data

US 2022/0309649 A1    Sep. 29, 2022

(51) Int. Cl.
*G06T 7/00* (2017.01)
*A61B 8/00* (2006.01)
(Continued)

(52) U.S. Cl.
CPC .......... *G06T 7/0012* (2013.01); *A61B 8/4444* (2013.01); *A61B 8/463* (2013.01);
(Continued)

(58) Field of Classification Search
CPC ............... G06T 7/0012; G06T 7/11; G06T 2207/10132; G06T 2207/20021; G06T 2207/20084; G06T 2207/20081; G06T 2207/30004; A61B 8/4444; A61B 8/463; A61B 8/5207; A61B 8/429; A61B 8/4488; A61B 8/462; G06F 3/14; G06F 3/147;
(Continued)

(56) References Cited

U.S. PATENT DOCUMENTS 10,540,769 B2    1/2020  Pintoffl
10,918,359 B2 *  2/2021  Auvray ................ A61B 8/5269
(Continued)

OTHER PUBLICATIONS

Meng et al., "Automatic Shadow Detection in 2D Ultrasound Images," Sep. 2018, Lecture Notes in Computer Science, DOI: 10.1007/978-3-030-00807-9_7, In book: Data Driven Treatment Response Assessment and Preterm, Perinatal, and Paediatric Image Analysis, 3 pages.
(Continued)

*Primary Examiner* — Edward F Urban
*Assistant Examiner* — Benedict E Lee (57) ABSTRACT

Various methods and systems are provided for individually analyzing a plurality of subregions within an ultrasound image for acoustic shadowing. In one embodiment, a method includes acquiring ultrasound data along a plurality of receive lines, generating an ultrasound image based on the ultrasound data, dividing the ultrasound image into a plurality of subregions, and individually analyzing each of the plurality of subregions for acoustic shadowing. The method includes detecting acoustic shadowing in one or more of the plurality of subregions, displaying the ultrasound image, and graphically indicating the one or more of the plurality of subregions in which the acoustic shadowing was detected on the ultrasound image while the ultrasound image is displayed on a display device.

14 Claims, 5 Drawing Sheets

(51) Int. Cl.
  *A61B 8/08* (2006.01)
  *G06F 3/14* (2006.01)
  *G06N 3/08* (2023.01)
  *G06T 7/11* (2017.01)

(52) U.S. Cl.
  CPC .............. *A61B 8/5207* (2013.01); *G06F 3/14* (2013.01); *G06N 3/08* (2013.01); *G06T 7/11* (2017.01); *G06T 2207/10132* (2013.01); *G06T 2207/20021* (2013.01); *G06T 2207/20084* (2013.01)

(58) Field of Classification Search
  CPC .......... G06N 3/08; G06N 3/0464; G06N 3/09; G09G 2354/00; G09G 5/377; G09G 2380/08
  See application file for complete search history.

(56) References Cited

U.S. PATENT DOCUMENTS

| | | | |
|---|---|---|---|
| 2014/0187947 A1* | 7/2014 | Hansegard | A61B 8/469 600/443 |
| 2016/0051230 A1* | 2/2016 | Yoo | A61B 8/469 600/440 |
| 2016/0317130 A1* | 11/2016 | Auvray | A61B 8/461 |
| 2018/0008233 A1* | 1/2018 | Pelissier | A61B 8/4488 |
| 2019/0328361 A1 | 10/2019 | Halmann | |
| 2022/0249061 A1* | 8/2022 | Carrascal | G06V 10/25 |

OTHER PUBLICATIONS

Yasutomi et al, "Shadow Detection for Ultrasound Images Using Unlabeled Data and Synthetic Shadows," Aug. 2019, arXiv:1908.01439, 2019arXiv190801439Y, 4 pages.

* cited by examiner

ULTRASOUND IMAGING SYSTEM AND METHOD FOR DETECTING ACOUSTIC SHADOWING

FIELD OF THE INVENTION

The subject matter disclosed herein relates generally to ultrasound imaging systems and methods for detecting acoustic shadowing

BACKGROUND OF THE INVENTION

Acquiring ultrasound images as part of a diagnostic ultrasound imaging procedure involves transmitting ultrasonic signals into the patient and detecting ultrasonic signals that are reflected and/or backscattered from structures within the patient. Ultrasound advantageously does not utilize ionizing radiation in order to generate diagnostic images. However, ultrasonic signals require a suitable transmission medium for effective transmission. For example, ultrasound signals do not propagate effectively through air or a vacuum. In order to increase the effectiveness with which ultrasound signals are transmitted into and received from a patient, clinicians typically apply a coupling gel to ultrasound probes that are used externally in order to increase the quality of the acoustic coupling between the ultrasound probe and the skin of the patient. It is additionally necessary for the clinician to apply an amount of pressure to the ultrasound probe in order to ensure adequate acoustic coupling for the acquisition of high-quality ultrasound images. It may be difficult or impossible to acquire high-quality ultrasound images if some or all of the elements in a transducer array of the ultrasound probe are not in acoustic contact with the patient. Having some or all of the face of the ultrasound probe in poor acoustic contact with the patient may result in ultrasound images with acoustic shadowing.

Another limitation of ultrasound imaging is that ultrasonic signals cannot effectively penetrate some high-density structures such as bone. As a result, it can be difficult or impossible to image some anatomical areas if they are obscured by bone or other high-density structures. For example, when performing a chest examination, the patient's ribs can obscure structures positioned below the ribs if some or all of the transducer array is positioned on top of one or more ribs. Improper probe positioning with respect to bones or other high-density structures may also result in ultrasound images with acoustic shadowing.

Acoustic shadowing is undesirable because the resulting images do not contain information, or only contain partial information, in the regions exhibiting acoustic shadowing. It is typically desirable to acquire ultrasound images without any acoustic shadowing in order to maximize the diagnostic usefulness of the ultrasound images.

For the reasons discussed above, it may be desirable to alert ultrasound clinicians when they are acquiring an image with acoustic shadowing. This is especially important in order to provide feedback to novice or relatively novice users. Conventional techniques have typically treated the detection of acoustic shadows as a segmentation problem that analyzes the whole ultrasound image for acoustic shadows. The conventional technique is computationally expensive and has a high risk for incorrectly identifying some non-acoustic shadow regions as acoustic shadows. There is a need for a faster and more accurate technique for detecting acoustic shadowing in ultrasound images.

For at least the reasons discussed hereinabove, there is a need for improved methods and ultrasound imaging systems for detecting acoustic shadowing in ultrasound images.

BRIEF DESCRIPTION

In an embodiment, a method includes acquiring, with an ultrasound probe, ultrasound data along a plurality of receive lines, generating an ultrasound image based on the ultrasound data, and dividing, with a processor, the ultrasound image into a plurality of subregions, where each of the plurality of subregions extends from a top of the ultrasound image to a bottom of the ultrasound image and corresponds to an adjacent subset of the plurality of receive lines. The method includes individually analyzing, with the processor, each of the plurality of subregions for acoustic shadowing, detecting, with the processor, acoustic shadowing in one or more of the plurality of subregions, displaying the ultrasound image on the display device and graphically indicating the one or more of the plurality of subregions in which the acoustic shadowing was detected on the ultrasound image while the ultrasound image is displayed on the display device.

In an embodiment, an ultrasound imaging system includes an ultrasound probe, a display device, and a processor in electronic communication with the ultrasound probe and the display device. The processor is configured to control the ultrasound probe to acquire ultrasound data along a plurality of receive lines, generate an ultrasound image based on the ultrasound data, divide the ultrasound image into a plurality of subregions, where each of the plurality of subregions extends from a top of the ultrasound image to a bottom of the ultrasound image and corresponds to an adjacent subset of the plurality of receive lines. The processor is configured to individually analyze each of the plurality of subregions for acoustic shadowing, display the ultrasound image on the display device, and graphically indicate, on the ultrasound image, each of the plurality of subregions in which acoustic shadowing was detected while the ultrasound image is displayed on the display device.

In an embodiment, a non-transitory computer readable medium having stored thereon, a computer program for execution on a processor, which when executed by the processor, results in the performance of steps including: controlling an ultrasound probe to acquire ultrasound data along a plurality of receive lines, generating an ultrasound image based on the ultrasound data, dividing the ultrasound image into a plurality of subregions, where each of the plurality of subregions extends from a top of the ultrasound image to a bottom of the ultrasound image and corresponds to an adjacent subset of the plurality of receive lines, individually analyzing each of the plurality of subregions for acoustic shadowing, detecting acoustic shadowing in one or more of the plurality of subregions, displaying the ultrasound image on a display device, and graphically indicating the one or more of the plurality of subregions in which the acoustic shadowing was detected on the ultrasound image while the ultrasound image is displayed on the display device.

BRIEF DESCRIPTION OF THE DRAWINGS

The inventive subject matter described herein will be better understood from reading the following description of non-limiting embodiments, with reference to the attached drawings, wherein below.

DETAILED DESCRIPTION

Figure 1:
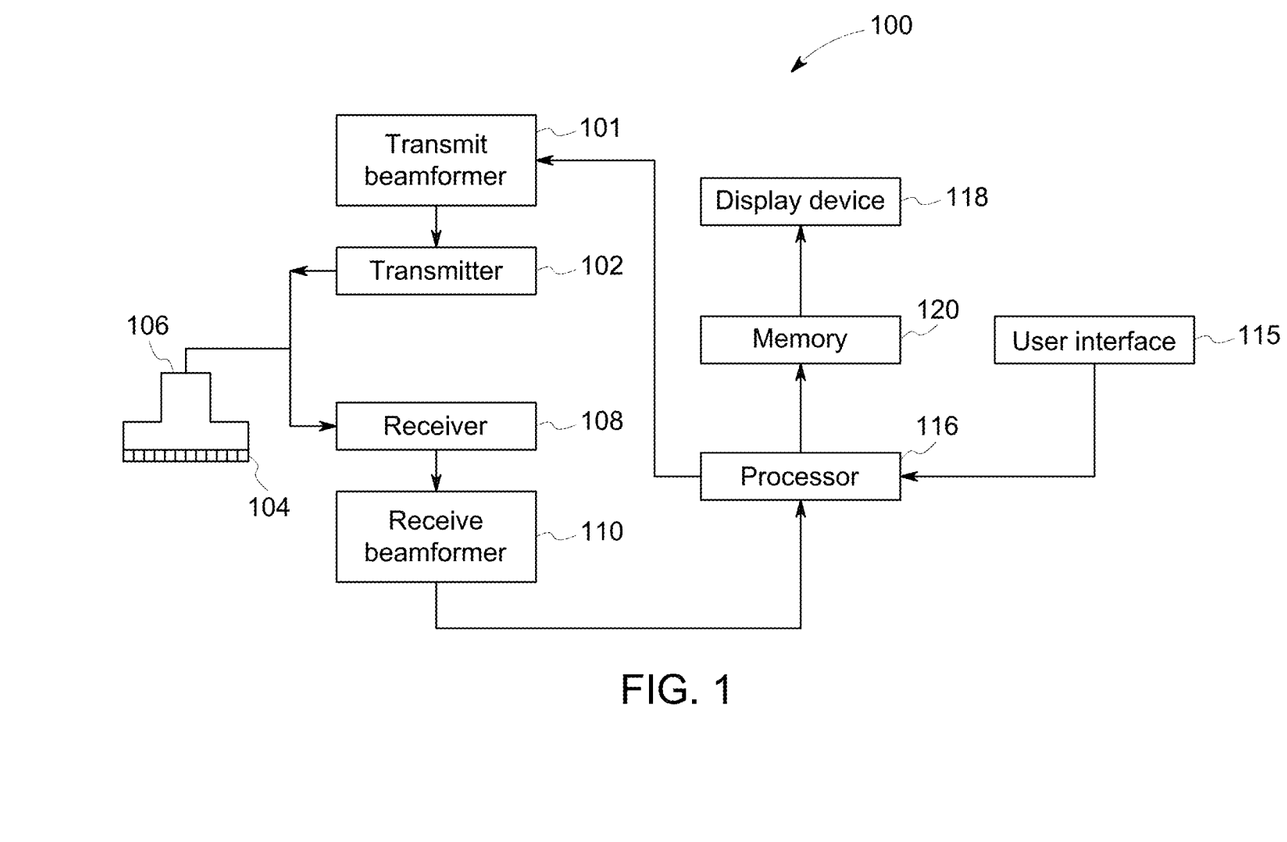
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within an ultrasound probe 106 to emit pulsed ultrasonic signals into a body (not shown) through one or more transmit events. The elements 104 may be arranged in an array. The ultrasound probe 106 may be linear array probe, a curved linear array probe, a phased array probe, a curved phased array probe, a 4D matrix array probe, or any other type of ultrasound probe. Still referring to FIG. 1, the pulsed ultrasonic signals are back-scattered from structures in the body, like blood cells or muscular tissue, to produce echoes that return to the elements 104. The echoes are converted into electrical signals by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit beamforming and/or the receive beamforming. For example, all or part of the transmit beamformer 101, the transmitter 102, the receiver 108 and the receive beamformer 110 may be situated within the ultrasound probe 106. The terms "scan" or "scanning" may also be used in this disclosure to refer to acquiring data through the process of transmitting and receiving ultrasonic signals. The terms "data" and "ultrasound data" may be used in this disclosure to refer to either one or more datasets acquired with an ultrasound imaging system. A user interface 115 may be used to control operation of the ultrasound imaging system 100. The user interface 115 may be used to control the input of patient data, or to select various modes, operations, parameters, and the like. The user interface 115 may include one or more user input devices such as a keyboard, hard keys, a touch pad, a touch screen, a track ball, rotary controls, sliders, soft keys, or any other user input devices.

The ultrasound imaging system 100 also includes a processor 116 to control the transmit beamformer 101, the transmitter 102, the receiver 108 and the receive beamformer 110. The user interface 115 is in electronic communication with the processor 116. The processor 116 may include one or more separate hardware components, such as a central processing unit (CPU), a microprocessor, a microcontroller, a graphics processing unit (GPU), a digital signal processor (DSP), combinations thereof, and the like. According to some embodiments, the processor 116 may include one or more GPUs, where some or all of the GPUs include a tensor processing unit (TPU). According to embodiments, the processor 116 may include a field-programmable gate array (FPGA), or any other type of hardware capable of carrying out processing functions. The processor 116 may be an integrated component or it may be distributed across various locations. For example, according to an embodiment, processing functions associated with the processor 116 may be split between two or more processors based on the type of operation. For example, embodiments may include a first processor configured to perform a first set of operations and a second, separate processor to perform a second set of operations. According to embodiments, the processor 116 may be configured to implement a neural network. The processor 116 may be configured to execute instructions accessed from a memory. For example, the instructions may be stored on a non-transitory computer readable medium configured for execution by the processor 116. According to an embodiment, the processor 116 is in electronic communication with the ultrasound probe 106, the receiver 108, the receive beamformer 110, the transmit beamformer 101, and the transmitter 102. For purposes of this disclosure, the term "electronic communication" may be defined to include both wired and wireless connections. The processor 116 may control the ultrasound probe 106 to acquire ultrasound data. The processor 116 controls which of the elements 104 are active and the shape of a beam emitted from the ultrasound probe 106. The processor 116 is also in electronic communication with a display device 118, and the processor 116 may process the ultrasound data into images for display on the display device 118. According to embodiments, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. The processor 116 may be configured to scan-convert the ultrasound data acquired with the ultrasound probe 106 so it may be displayed on the display device 118. Displaying ultrasound data in real-time may involve displaying the ultrasound data without any intentional delay. For example, the processor 116 may display each updated image frame as soon as each updated image frame of ultrasound data has been acquired and processed for display during the display of a real-time image. Real-time frame rates may vary based on the size of the region or volume from which data is acquired and the specific parameters used during the acquisition. According to other embodiments, the data may be stored temporarily in a buffer (not shown) during a scanning session and processed in less than real-time. According to embodiments that include a software beamformer, the functions associated with the transmit beamformer 101 and/or the receive beamformer 108 may be performed by the processor 116.

According to an embodiment, the ultrasound imaging system 100 may continuously acquire ultrasound data at a frame-rate of, for example, 10 Hz to 30 Hz. Images generated from the data may be refreshed at a similar frame-rate. Other embodiments may acquire and display data at different rates. For example, some embodiments may acquire ultrasound data at a frame rate of less than 10 Hz or greater than 30 Hz depending on the size of each frame of data and the parameters associated with the specific application. For example, many applications involve acquiring ultrasound data at a frame rate of about 50 Hz. A memory 120 is included for storing processed frames of acquired data. In an exemplary embodiment, the memory 120 is of sufficient capacity to store frames of ultrasound data acquired over a period of time at least several seconds in length. The frames of data are stored in a manner to facilitate retrieval thereof according to its order or time of acquisition. The memory 120 may comprise any known data storage medium.

In various embodiments of the present invention, data may be processed by other or different mode-related modules by the processor 116 (e.g., B-mode, color Doppler, M-mode, color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored, and timing information indicating a time at which the data was acquired in memory may be recorded. The modules may include, for example, a scan conversion module to perform scan conversion operations to convert the image frames from beam space coordinates to display space coordinates. A video processor module may be provided that reads the image frames from a memory, such as the memory 120, and displays the ultrasound image frames in real-time while a procedure is being carried out on a patient. The video processor module may store the image frames in an image memory, from which the images are read and displayed.

Figure 2:
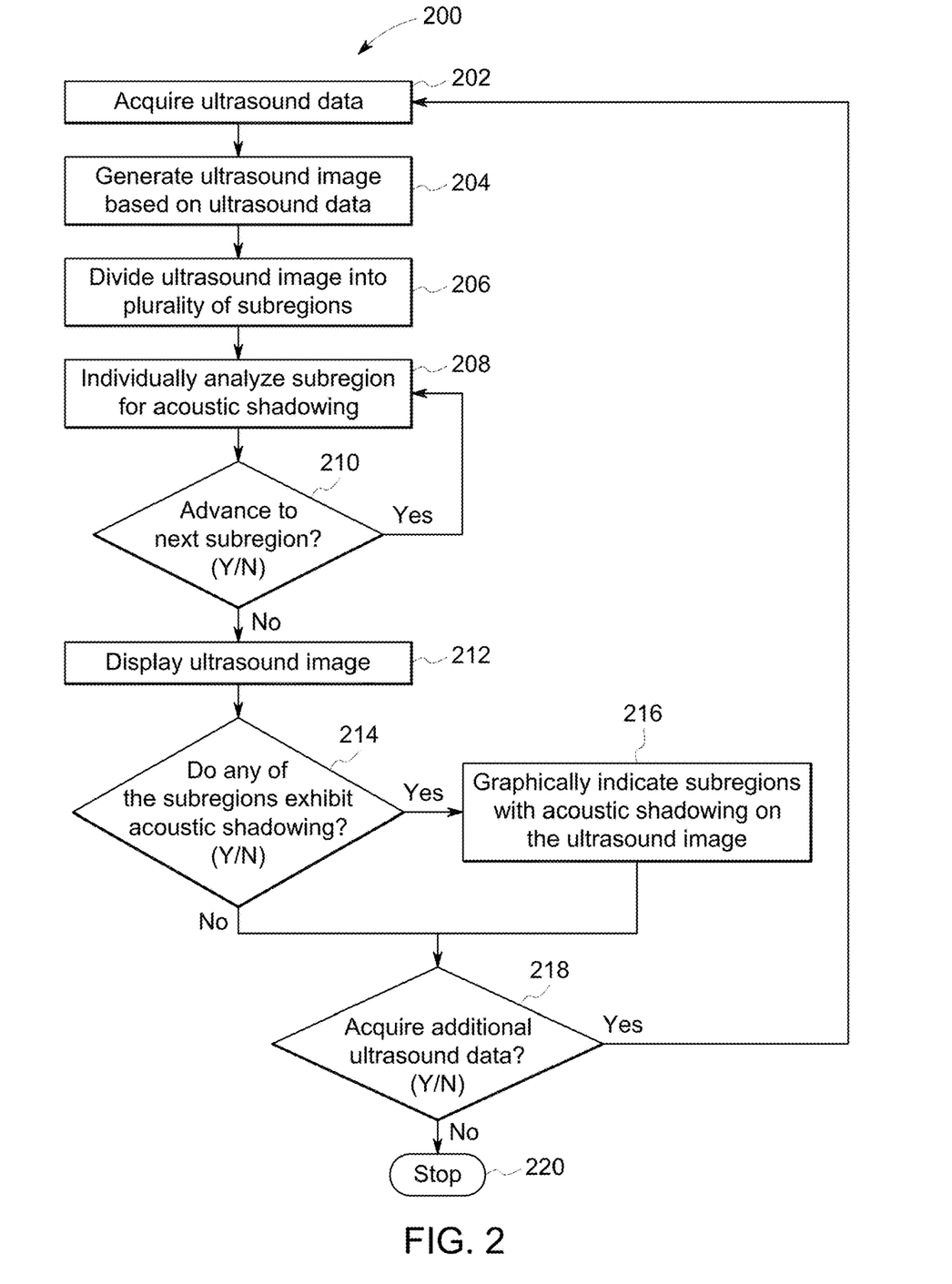
FIG. 2 is a flow chart in accordance with an embodiment.

FIG. 2 illustrates a flowchart of one embodiment of a method 200 for analyzing an ultrasound image for acoustic shadowing. The method 200 shown in FIG. 2 may be performed with the ultrasound imaging system 100 shown in FIG. 1. The technical effect of the method 200 is the graphical indication of one or more of a plurality of subregions in the ultrasound image in which acoustic shadowing was detected based on an individual analysis of each of the plurality of subregions.

At step 202, the processor 116 controls the ultrasound probe 106 to acquire ultrasound data. In the process of controlling the ultrasound probe 106 to acquire ultrasound data, the processor 116 also controls the transmit beamformer 101, the transmitter 102, the receiver 108 and the receive beamformer 110.

Figure 3:
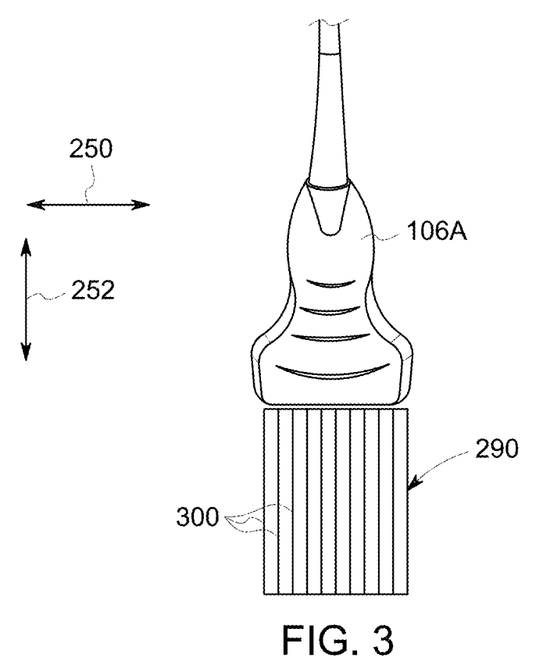
FIG. 3 illustrates a linear array probe and a field-of-view in accordance with an embodiment.

FIG. 3 is an illustration of an embodiment where the ultrasound probe is a linear array probe. FIG. 3 includes a linear array probe 106A and a field-of-view 290 associated with the linear array probe 106A. According to an embodiment, the processor 116 controls the linear array probe 106A to acquire ultrasound data along a plurality of receive lines 300. Each of the receive lines 300 is oriented in a perpendicular orientation with respect to the transducer array in the linear array probe 106A. An azimuthal direction 250 and a depth direction 252 is shown with respect to the probe 106A. The azimuthal direction 250 is parallel to a face of the transducer array in the probe 106A and the depth direction 252 is perpendicular to the azimuthal direction 250. Each of the receive lines 300 in FIG. 3 is parallel to the depth direction 252.

Figure 4:
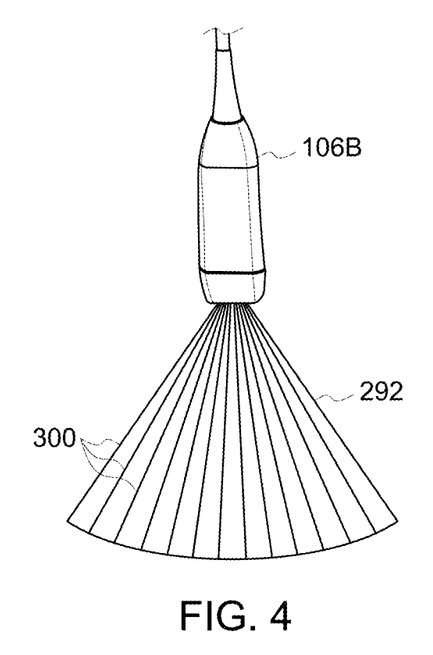
FIG. 4 illustrates a phased array probe and a field-of-view in accordance with an embodiment.

FIG. 4 is an illustration of an embodiment where the ultrasound probe is a phased array probe. FIG. 4 includes a phased array probe 106B and a field-of-view 292 associated with the linear array probe 106B. According to an embodiment, the processor 116 control the linear array probe 106B to acquire ultrasound data along a plurality of receive lines 300. The field-of-view 292 of the phased array probe 106B is a different shape than the field-of-view 290 of the linear array probe 106A shown in FIG. 1. The phased array probe 106B controls the relative phasing of the elements in the transducer array in order to steer the emitted ultrasonic signals. As such, not all of the receive lines 300 are perpendicular with respect to the transducer array in the phased array probe 106B.

Figure 5:
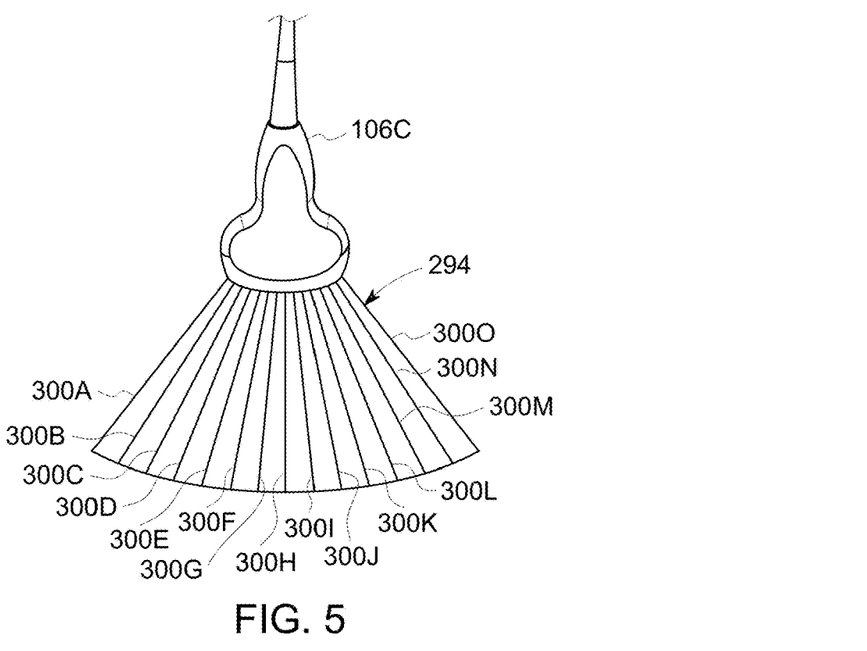
FIG. 5 illustrates a curved linear array probe and a field-of-view in accordance with an embodiment.

FIG. 5 is an illustration of an embodiment where the ultrasound probe 106 is a curved linear array probe. FIG. 5 includes a curved linear array probe 106C and a field-of-view 294 associated with the curved linear array probe 106C. According to an embodiment, the processor 116 may control the curved linear array probe 106C to acquire ultrasound data along a plurality of receive lines 300. Each of the receive lines 300 may be oriented in a perpendicular orientation with respect to the transducer array in the curved linear array probe 106A according to an embodiment.

The method 200 will be described in accordance with an exemplary embodiment where the ultrasound probe 106 is a curved linear array probe, such as the curved linear array probe 106C shown in FIG. 5. It should be appreciated that the method 200 may be performed using different types of ultrasound probes, such as, but not limited to, a linear array probe such as the linear array probe 106A shown in FIG. 3, or a phased array probe such as the phased array probe 106B shown in FIG. 4.

Referring back to the method 200, at step 202 the processor 116 may control the ultrasound probe 106 to emit either focused or unfocused transmit events and then acquire ultrasound data along the plurality of receive lines 300. The processor 116 may, for instance, control the ultrasound probe 106 to focus a subset of the elements 104 in the transducer array to receive data along a consecutive series of points, or samples, along each of the receive lines 300. According to one acquisition scheme, the processor 116 may start by acquiring samples at the maximum depth along a receive line and then consecutively acquiring samples at shallower depths along that receive line. After acquiring all the samples along a first receive line, the processor 116 may control the ultrasound probe 106 to acquire samples along a different receive line. FIG. 5 includes a first receive line 300A, a second receive line 300B, a third receive line 300C, a fourth receive line 300D, a fifth receive line 300E, a sixth receive line 300F, a seventh receive line 300G, an eight receive line 300H, a ninth receive line 300I, a tenth receive line 300J, an eleventh receive line 300K, a twelfth receive line 300L, a thirteenth receive line 300M, a fourteenth receive line 300N, and a fifteenth receive line 300O. It should be appreciated that while FIG. 5 schematically represents 15 receive lines 300, other embodiment could use either more than 15 receive lines per ultrasound image or less than 15 receive lines per ultrasound image. It is expected that most embodiments will use more than 15 receive lines per ultrasound image.

The processor 116 may acquire ultrasound data along the plurality of receive lines 300 according to many different acquisition schemes. According to one scheme, the processor 116 may acquire ultrasound data in raster pattern across the field-of-view 294. For example, the processor may first acquire ultrasound data along the first receive line 300A and then advance to the next adjacent receive line, which is the second receive line 300B. After acquiring ultrasound data along the second receive line 300B, the processor 116 may control the ultrasound probe 106 to acquire ultrasound data along the third receive line 300C, and so forth until ultrasound data has been acquired from all of the receive lines in the field-of-view 294. After acquiring an ultrasound image, or frame, the processor 116 may repeat the pattern of acquiring ultrasound data along each of the receive lines 300 in the same or a different order in order to acquire a next frame in order to acquire a plurality of frames during a live or cine acquisition.

Next, at step 204, the processor 116 generates an ultrasound image based on the ultrasound data acquired at step 202. According to an embodiment, the ultrasound image may be generated based on the data acquired along all of the plurality of receive lines 300 in the field-of-view 294. According to an embodiment, the processor 116 may scan-convert the ultrasound data into a format suitable for display.

Figure 6:
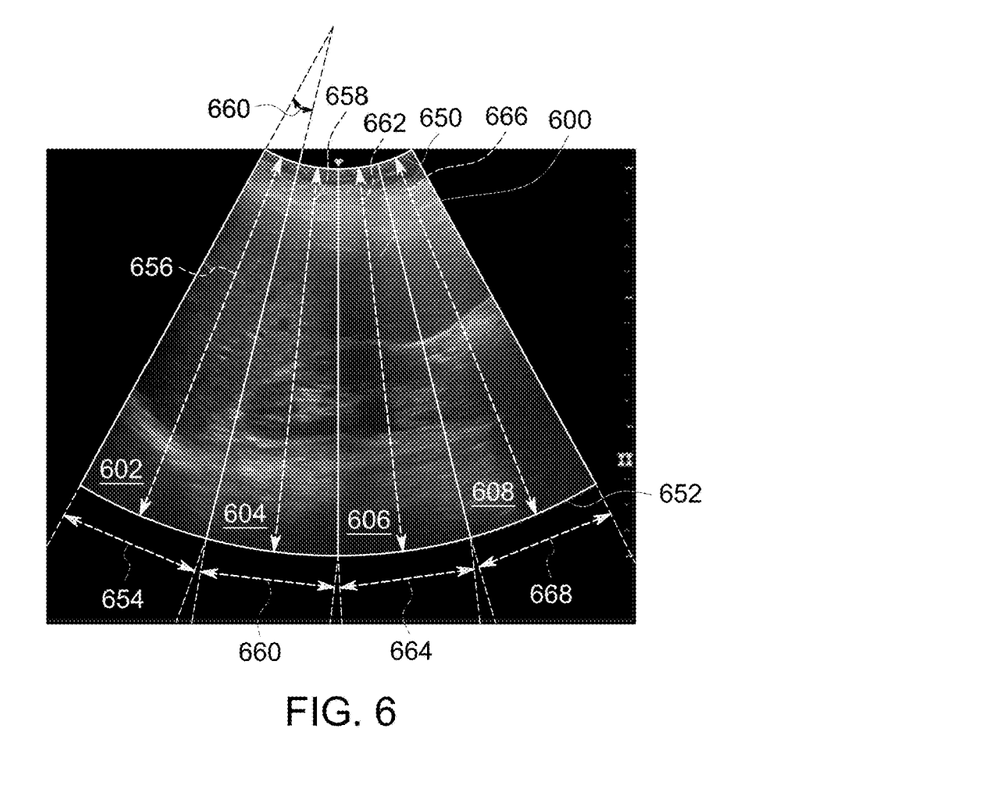
FIG. 6 illustrates an ultrasound image in accordance with an embodiment.

At step 206, the processor 116 divides the ultrasound image into a plurality of subregions. FIG. 6 shows an ultrasound image 600 in accordance with an exemplary embodiment. A plurality of subregions are represented on the ultrasound image 600. For example, FIG. 6 includes a first subregion 602, a second subregion 604, a third subregion 606, and a fourth subregion 608. Each of the subregions extends from a top of the ultrasound image 650 to a bottom of the ultrasound image 652. The top of the ultrasound image 650 is the portion of the ultrasound image 650 closest to the ultrasound probe 106 while the bottom of the ultrasound image 652 is the portion of the ultrasound image furthest from the ultrasound probe 106 in a depth direction, which is measured in a direction perpendicular to the transducer array 104 in the ultrasound probe 106. Each of the subregions extends the entire height of the ultrasound image 600 in the depth direction. In the embodiment shown in FIG. 6, each of the subregions has an angle. An angle 660 of the first subregion 602 is illustrated on FIG. 6. The angle of each of the subregions may be the same, or one or more of the subregions may have a different angle from the other subregions.

Each of the plurality of subregions corresponds to an adjacent subset of the receive lines. For example, the first subregion 602 may correspond to receive lines 300A, 300B, 300C, 300D, and 300E; the second subregion 604 may correspond to receive lines 300E, 300F, 300G, 300H, and 300I; the third subregion 606 may correspond to receive lines 300I, 300J, 300K, and 300L; the fourth subregion 608 may correspond to receive lines 300L, 300M, 300N, and 300O.

Each of the subregions corresponds to a subset of the receive lines used during the acquisition of the ultrasound data. The shape of the subregions is based on the positions of the receive lines used to acquire the ultrasound data in each of the respective subregions. Each of the subregions may be composed of an adjacent subset of the receive lines. For many acquisition geometries, this results subregions with a shape generally similar to the field-of-view, but with a narrower width in the azimuthal (i.e., lateral) direction. Each of the subregions has the same depth as the field-of-view. Each field-of-view may be split into a plurality of similar subregions. It may be advantageous to have some or all of the subregions partially overlap with adjacent subregions. For example, in the embodiment discussed with respect to FIGS. 5 and 6, the second subregion 604 overlaps with the first subregion 602 and the third subregion 606; and the third subregion 606 overlaps with the second subregion 604 and the fourth subregion 608. In other embodiments, the subregions may overlap an adjacent subregion by more than one receive line. Or, in other embodiments, adjacent subregions may not overlap at all. One or more receive lines used to acquire the ultrasound data may be in both of the overlapping subregions. While an exemplary embodiment with four subregions has been described with respect to FIG. 5, it should be appreciated that in other embodiments the processor 116 may divide the ultrasound image into a different number of subregions. For example, the processor 116 may divide the ultrasound image into fewer than four subregions or more than four subregions according to various embodiments.

By having the subregions correspond to an adjacent subset of the plurality of receive lines 300, the geometry of each subregion makes use of an acoustic path between the ultrasound probe 106 and the patient being scanned. According to some embodiments, it may be advantageous to use subregions that are significantly longer in a depth direction, which is perpendicular to the transducer array, than in an azimuthal direction, which is along the direction of the transducer array. According to an embodiment, each of the plurality of subregions may have an angle of less than 15 degrees. According to an embodiment, each of the plurality of subregions may have an angle of less than 10 degrees. According to an embodiment, each of the plurality of subregions may have an angle of less than 5 degrees. According to an embodiment, each of the subregions may have a depth-to-width ratio of 5:1 or greater, where the depth is the length in the depth direction and the width is the maximum width in the azimuthal direction. For example, the first subregion 602 has a length 656 in the depth direction and a maximum width 654 in the azimuthal direction. The second subregion 604 has a length 658 in the depth direction and a maximum width 660 in the azimuthal direction. The third subregion 606 has a length 662 in the depth direction and a maximum width 664 in the azimuthal direction. And, the fourth subregion 608 has a length 666 in the depth direction and a maximum width 668 in the azimuthal direction. According to an embodiment, each of the subregions may have a depth-to-width ratio of 3:1 or greater. In other embodiments, each of the subregions may have a depth-to-width ratio of 5:1 or greater. For example, the first subregion 602 in FIG. 6 has a depth-to-width ratio that is the ratio of the length 656 to the maximum width 654. The second subregion 604 has a depth-to-width ratio that is the ratio of the length 658 to the maximum width 660. The third subregion 606 has a depth-to-width ratio that is the ratio of the length 662 to the maximum width 664. And, the fourth subregion 608 has a depth-to-width ratio that is the ratio of the length 666 to the maximum width 668.

Next, at step 208, the processor 116 individually analyzes one of the subregions for acoustic shadowing. At step 210, the processor 116 determines if it should advance to the next subregion. If it is not desirable to advance to the next subregion, the method 200 advances to step 212. If it is desirable to advance to the next subregion, the method returns to step 208 and individually analyzes the next subregion for acoustic shadowing. According to an embodiment, the method 200 may iteratively repeat steps 208 and 210 in order to individually analyze the first subregion 602, then the second subregion 604, then the third subregion 606, then the fourth subregion 608. It should be appreciated that the method 200 may individually analyze each of the subregions for acoustic shadowing in a different order according to various embodiments.

At step 208, the processor 116 individually analyzes one of the subregions for acoustic shadowing. Unlike conventional techniques, the processor 116 is not attempting to segment regions of acoustic shadowing. Instead, the processor 116 is configured to simply determine whether or not each subregion exhibits acoustic shadowing. Solving a classification problem, such as whether or not each subregion exhibits acoustic shadowing, is computationally easier and more robust than solving an image segmentation problem, such as segmenting an acoustic shadow region, as is performed by conventional solutions. The network architecture used, for example, with a deep learning network, may be much simpler and more compact for solving a classification problem compared to solving an image segmentation problem. As such, it is possible to use a simpler network to solve a classification problem. For example, compared to the network needed to solve an image segmentation problem, the network needed to solve a classification problem may have one or more of fewer layers, fewer nodes, a smaller footprint, and/or use rely on simpler processor in order to implement the network. This provides advantages in terms of both the overall cost and complexity of the network and may enable the network to be run either more quickly or as quickly with reduced processing power. For a given amount of processing power, the classification technique of the current invention will run more quickly than the segmentation technique of conventional systems.

Additionally, since the present invention relies on a classification of each subregion, it is not necessary to accurately delineate the shadow region in the training images. This reduces the annotation burden in order to train the network in order to detect the acoustic shadowing in each of the subregions. As a general rule, solving classification problems, such as whether or not each subregion exhibits acoustic shadowing, is considered easier to learn (i.e., it is easier to accurately train the network) than solving image segmentation problems. In most circumstances, performing a classification of each subregion will therefore be more robust than attempting to segment one or more acoustic shadow regions from the image.

The processor 116 may be configured to implement a deep learning network in order to analyze the subregion for acoustic shadowing at step 208. Examples of deep learning networks include a convolutional neural network (CNN), a fully connected network (FCN), a deep neural network (DNN), a random forest, a support vector machine (SVM), and so forth. According to an exemplary embodiment, the deep learning network may include a neural network such as a convolutional neural network (CNN). Embodiments may use multiple neural networks or multiple convolutional neural networks.

The deep learning network may be trained in order to identify acoustic shadowing, which could be the result of poor probe contact with the patient or from one or more dense structure/s within the patient preventing the ultrasonic energy from penetrating below the depth of the dense structure. For example, bones such as ribs commonly cause acoustic shadowing when attempting to image a portion of the patient's thoracic chamber, such as when performing lung imaging.

The deep learning network may be trained based on a curated set of ultrasound images or a curated set of subregions. For example, the ultrasound images or subregions may have one or more acoustic shadow regions identified on each of the ultrasound images. The deep learning network may then either be trained based on subregions generated based on the curated ultrasound images or the deep learning network may be trained using a curated set of subregions that were generated from a set of ultrasound images. The deep learning network is being trained to make a binary decision about each subregion. The deep learning network is trained to indicate either that the subregion does not exhibit acoustic shadowing or that the subregion does exhibit acoustic shadowing. By using a classification-based approach rather than a segmentation-based approach, the technique of the present invention should be more computationally efficient than conventional techniques. Using a more computationally efficient technique may provide one or more of the following advantages: the technique of method 200 may be implemented using reduced computational resources compared to conventional techniques; and/or the technique of the method 200 may be performed more quickly compared to conventional techniques. As such, the method 200 is well-suited for real-time use while acquiring a live or cine image. Additionally, the method 200 is well-suited for use on portable ultrasound imaging systems, hand-held ultrasound imaging systems, or hand-carried ultrasound imaging systems.

It is known that acoustic shadows are formed along the length of the receive lines. For example, if acoustic shadowing is caused by either lack of probe contact the entire receive line corresponding to the portion of the probe 106 that is not in contact will be an acoustic shadow. If acoustic shadowing is caused by an acoustically dense structure, such as bone, the entire receive line at depths below the acoustically dense structure will be an acoustic shadow. In the present invention, each subregion is shaped based on a subset of adjacent receive lines. Each subregion is smaller than the entire image and shaped to help the processor 116 detect acoustic shadowing more efficiently. Since acoustic shadows fall along the length of the receive lines, having the subregions shaped to include an adjacent subset of the receive lines allows for an easier classification task by the processor 116. For example, if there is any acoustic shadowing, it is known that the acoustic shadowing will be shaped along the receive lines. Shaping the subregions along the receive lines helps achieve better performance in terms of detection accuracy by ensuring that any detected shadows are aligned with the receive lines. The use of subregions allows only the shadow-specific context to be provided to the algorithm instead of the full image. As such, the detection technique used by the processor 116 may be generalized across different types of ultrasound imaging systems and applications.

At step 212, the processor 116 is configured to display the ultrasound image generated at step 204 on the display device 118. At step 214, the processor 116 determines if any of the subregions exhibit acoustic shadowing, as determined during the multiple iterations of performing step 208. If none of the subregions exhibit acoustic shadowing, the method 200 advances to step 218. If one or more of the subregions exhibit acoustic shadowing, the method advances to step 216 where the processor 116 graphically indicates the one or more of the subregions in which the acoustic shadowing was detected. According to other embodiments, the processor 116 may first analyze each of the subregions for evidence of acoustic shadowing and then, after all of the subregions have been analyzed, the processor 116 may graphically indicate any of the subregions that were determined to have exhibited evidence of acoustic shadowing.

Figure 7:
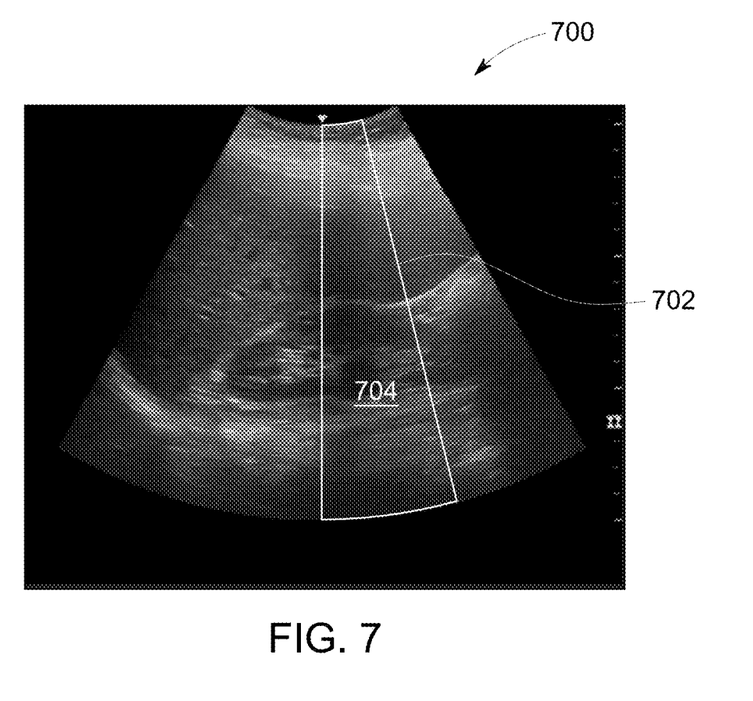
FIG. 7 illustrates an ultrasound image in accordance with an embodiment.

According to an embodiment, the processor 116 may graphically indicate one or more of the subregions in which the acoustic shadowing was detected by displaying a boundary around some or all of each of the one or more subregions in which the acoustic shadowing was detected. For example, FIG. 7 shows an illustration of an image 700 with one of the subregions indicated with a boundary 702. The boundary 702 clearly indicates to the clinician that there is acoustic shadowing in the subregion 704 surrounded by the boundary 702. The boundary may be displayed in a color to visually distinguish it from the ultrasound image.

Figure 8:
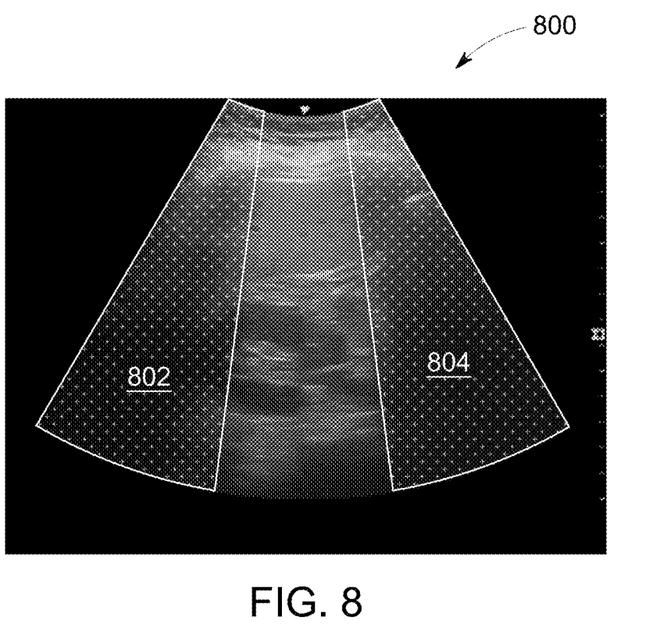
FIG. 8 illustrates an ultrasound image in accordance with an embodiment.

According to an embodiment, the processor 116 may graphically indicate one or more of the subregions in which the acoustic shadowing was detected by highlighting each of the one or more subregions in which the acoustic shadowing was detected. For example, FIG. 8 shows an illustration of an ultrasound image 800 with two subregions highlighted. A first highlighted region 802 indicates that acoustic shadowing was detected in the subregion corresponding to the first highlighted region 802. A second highlighted region 804 indicates that acoustic shadowing was detected in the subregion corresponding to the second highlighted region 804. Hatching is used on FIG. 8 to indicate the highlighted regions 802 and 804. The highlighting may be performed using any color in order to distinguish the subregion in which the acoustic shadowing was detected from the rest of the ultrasound image.

At step 218, if it is desired to acquire additional ultrasound data, the method returns to step 202. If it is not desired to acquire additional ultrasound data at step 218, the method 200 advances to step 220 and stops.

The technique described in this disclosure has many advantages over conventional techniques: it is faster to run, easier to the train the network, and it offers a more-robust identification of acoustic shadowing. Also, by providing the clinician with real-time feedback, in the form of graphically indicating the one or more subregions where acoustic shadowing was detected, the current technique allows the clinician to quickly take corrective action. For example, upon seeing graphical indication of one or ore subregions with acoustic shadowing, the clinician may move or reposition the ultrasound probe 106 and/or apply more pressure until the images acquired with the ultrasound probe 106 do not include any evidence of acoustic shadowing. As described hereinabove, using subregions that represent an adjacent subset of receive lines helps enable more efficient classification of receive lines. Having subregions that are significantly longer in a depth direction than they are wide in a lateral direction makes each subregion mirror the dimensions of any expected acoustic shadowing. Since acoustic shadowing propagates along the receive lines (i.e., if there is an acoustic obstruction or if the probe is not in good acoustic contact, the entire receive line beneath that point will be an acoustic shadow), any evidence of acoustic shadowing will tend to be longer in a depth direction than it is wide in an azimuthal direction. For these reasons, it is more efficient to categorize a plurality of subregions that are each narrower than the ultrasound image in a lateral (i.e., azimuthal direction) compared to segmenting acoustic shadow regions from an entire image.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method comprising:
acquiring, with an ultrasound probe, ultrasound data along a plurality of receive lines, wherein the ultrasound probe is one of a curved linear array probe or a curved phased array probe;
generating an ultrasound image based on the ultrasound data;
dividing, with a processor, the ultrasound image into a plurality of subregions, where each of the plurality of subregions extends from a top of the ultrasound image to a bottom of the ultrasound image and corresponds to an adjacent subset of the plurality of receive lines, wherein each the plurality of subregions has an angle of less than 15 degrees;
individually analyzing, with the processor, each of the plurality of subregions for acoustic shadowing;
detecting, with the processor, acoustic shadowing in one or more of the plurality of subregions;
displaying the ultrasound image on a display device; and
graphically indicating the one or more of the plurality of subregions in which the acoustic shadowing was detected on the ultrasound image while the ultrasound image is displayed on the display device.

2. The method of claim 1, wherein each of the plurality of subregions has an angle of less than 10 degrees.

3. The method of claim 1, wherein each of the plurality of subregions partially overlaps an adjacent one of the plurality of subregions.

4. The method of claim 1, wherein said individually analyzing each of the plurality of subregions for acoustic shadowing comprises implementing a deep learning network with the processor.

5. The method of claim 4, wherein the deep learning network comprises a convolutional neural network (CNN).

6. The method of claim 1, wherein said graphically indicating comprises displaying a boundary of the one or more of the plurality of subregions in which the acoustic shadowing was detected.

7. The method of claim 6, wherein the ultrasound image is a grey-scale image and the boundary is displayed in a color.

8. The method of claim 1, wherein said graphically indicating comprises highlighting the one or more of the plurality of subregions in which the acoustic shadowing was detected.

9. An ultrasound imaging system comprising:
an ultrasound probe, wherein the ultrasound probe is one of a curved linear array probe or a curved phased array probe;

a display device; and
a processor in electronic communication with the ultrasound probe and the display device, wherein the processor is configured to:
  control the ultrasound probe to acquire ultrasound data along a plurality of receive lines;
  generate an ultrasound image based on the ultrasound data;
  divide the ultrasound image into a plurality of subregions, where each of the plurality of subregions extends from a top of the ultrasound image to a bottom of the ultrasound image and corresponds to an adjacent subset of the plurality of receive lines, wherein each of the plurality of subregions has an angle of less than 15 degrees;
  individually analyze each of the plurality of subregions for acoustic shadowing;
  display the ultrasound image on the display device; and
  graphically indicate, on the ultrasound image, each of the plurality of subregions in which acoustic shadowing was detected while the ultrasound image is displayed on the display device.

10. The ultrasound imaging system of claim 9, wherein the processor is configured to implement a deep learning network in order to individually analyze each of the plurality of subregions.

11. The ultrasound imaging system of claim 10, wherein the deep learning network is a convolutional neural network (CNN).

12. The ultrasound imaging system of claim 9, wherein the processor is configured to graphically indicate each of the plurality of subregions in which acoustic shadowing was detected by displaying a boundary of the plurality of subregions in which acoustic shadowing was detected.

13. The ultrasound imaging system of claim 12, wherein the boundary is colorized.

14. The ultrasound imaging system of claim 9, wherein the processor is configured to graphically indicate each of the plurality of subregions in which acoustic shadowing was detected by highlighting each of the plurality of subregions in which acoustic shadowing was detected.

* * * * *